United States Patent
Ji et al.

(10) Patent No.: US 9,115,154 B1
(45) Date of Patent: Aug. 25, 2015

(54) METHOD OF PREPARING TRIS-(2-CHLOROETHYL)PHOSPHITE

(71) Applicant: SHAOXING EASTLAKE BIOCHEMICAL CO., LTD., Zhejiang (CN)

(72) Inventors: Guoyan Ji, Zhejiang (CN); Chengrong Ding, Zhejiang (CN); Guofu Zhang, Zhejiang (CN); Sheng Ji, Zhejiang (CN); Guoyao Ji, Zhejiang (CN); Xiaoying Ji, Zhejiang (CN); Huadong Yang, Zhejiang (CN)

(73) Assignee: SHAOXING EASTLAKE BIOCHEMICAL CO., LTD., Shaoxing, Zheijiang (CN)

( * ) Notice: Subject to any disclaimer, the term of this patent is extended or adjusted under 35 U.S.C. 154(b) by 0 days.

(21) Appl. No.: 14/706,227

(22) Filed: May 7, 2015

(30) Foreign Application Priority Data

Jul. 15, 2014 (CN) .......................... 2014 1 0335652

(51) Int. Cl.
*C07F 9/141* (2006.01)

(52) U.S. Cl.
CPC ...................................... *C07F 9/141* (2013.01)

(58) Field of Classification Search
USPC ............................................................ 558/91
See application file for complete search history.

(56) References Cited

U.S. PATENT DOCUMENTS 3,888,953 A * 6/1975 Anderson et al. ............... 558/91

* cited by examiner

*Primary Examiner* — Kristin Vajda
(74) *Attorney, Agent, or Firm* — Workman Nydegger

(57) ABSTRACT

The present disclosure discloses a method of preparing tris-(2-chloroethyl)phosphite, comprising: continuously pumping phosphorus trichloride and ethylene oxide into a tubular pre-mixer for pre-mixing, respectively, and starting a refrigerant cooling unit of the microchannel reaction device simultaneously, to obtain a product tris-(2-chloroethyl)phosphite after complete reaction. The method according to the present disclosure not only significantly improves the content of the esterification product, thus increasing the production efficiency by 10 to 100 times than that of an ordinary tank reactor, but also reduces the residence time of the esterification product in the reactor from 110 hours to several minutes.

10 Claims, 2 Drawing Sheets

METHOD OF PREPARING TRIS-(2-CHLOROETHYL)PHOSPHITE

FIELD OF THE INVENTION

The present disclosure relates to a method of preparing tris-(2-chloroethyl)phosphite, and in particular to a method of preparing tris-(2-chloroethyl)phosphite by means of microchannel reaction technology.

BACKGROUND OF THE INVENTION

Tris-(2-chloroethyl)phosphite is an important intermediate of ethephon, which is a plant growth regulator. At present, the common method used to produce tris-(2-chloroethyl)phosphite comprises the following steps: to a reactor with phosphorus trichloride, the vaporized ethylene oxide gas was introduced into the liquid phosphorus trichloride and the reaction was performed as shown by the following reaction formula:

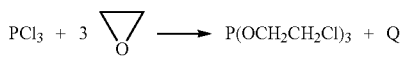

and the temperature was controlled from 45 to 50° C.

The above reaction is a strong exothermic reaction. Currently, the esterfication reaction of phosphorus trichloride and ethylene oxide is carried out in an ordinary enamel reactor, and thus there are several issues invovled. On the one hand, because the above-mentioned esterfication is a strong exothermic reaction and the heat exchange area of the enamel reactor is very limited, the aeration rate of ethylene oxide is restricted. In a 2000 L reactor, the aeration rate of ethylene oxide can only achieve 5-15 kg/h. As a result, it will take 110 hours to prepare one batch of tris-(2-chloroethyl)phosphite. Therefore, the production efficiency is very low. On the other hand, since the product tris-(2-chloroethyl)phosphite is not stable, it will involve side reactions while reaction system remains at 45° C.-50° C. for a long time. At the same time, because of long-term contaction between moist air and the raw material phosphorus trichloride, a series of side reactions, such as oxidation and hydrolysis will arise. Consequently, the purity of tris-(2-chloroethyl)phosphite obtained from the above process only achieves about 90%. Therefore the production efficiency suffers as a result and the active ingredients in ethephon is restricted seriously.

SUMMARY OF THE INVENTION

The present disclosure aims to provide an efficient, low cost, and industrially-valuable new method of producing tris-(2-chloroethyl)phosphite, to solve the problems existing in the prior art.

The present disclosure provides a method of preparing tris-(2-chloroethyl)phosphite using microchannel technology, comprising the steps of:
(1) continuously pumping phosphorus trichloride and ethylene oxide into a tubular pre-mixer for pre-mixing, respectively, at a mixing pressure in a range from 0.01 MPa to 2.00 MPa, to achieve sufficient mixing of the phosphorus trichloride and the ethylene oxide; and
(2) introducing the pre-mixed mixture of the phosphorus trichloride and the ethylene oxide into a microchannel reaction device, and starting a refrigerant cooling unit of the microchannel reaction device simultaneously, to obtain a product tris-(2-chloroethyl)phosphite after complete reaction.

In one preferred embodiment of the present disclosure, the microchannel reaction device comprises a plurality of, preferably 1 to 10 sets of, microchannel reactors connected in series with each other. In a further preferred embodiment, each microchannel reactor comprises 50 to 500 pipes. In a further preferred embodiment, each pipe is a straight pipe having a size of Ø4 mm×2000 mm. In particular, in the present disclosure, each pipe circles within the microchannel reactor, which has a diameter of 600 mm and a length of 2000 mm. More preferably, the microchannel reaction device comprises 3 to 5 sets of microchannel reactors connected in series with each other, each set of the microchannel reactors comprising 100 to 300 pipes each having a size of Ø4 mm×2000 mm.

In one preferred embodiment of the present disclosure, the residence time of the mixture of the phosphorus trichloride and the ethylene oxide in the microchannel reaction device ranges from 1 min to 5 min.

In one preferred embodiment of the present disclosure, the temperature of the materials, the pressure, and the molar ratio of the phosphorus trichloride to the ethylene oxide in the microchannel reaction device range from 0° C. to 50° C., 0.01 MPa to 2.00 MPa, and 1:3.0 to 1:3.8, respectively.

In one preferred embodiment of the present disclosure, the tubular pre-mixer comprises at least a static mixing pipe. The static mixing pipe having a size of Ø50 mm×1000 mm is preferably used.

In one preferred embodiment of the present disclosure, the phosphorus trichloride enters the tubular pre-mixer at a flow rate ranging from 100 kg/h to 1000 kg/h, preferably from 200 kg/h to 600 kg/h; and the ethylene oxide enters the tubular pre-mixer at a flow rate ranging from 100 kg/h to 1000 kg/h, preferably from 200 kg/h to 600 kg/h.

In one preferred embodiment of the present disclosure, the reaction pressure and the reaction temperature range from 0.30 MPa to 0.80 MPa, and 15° C. to 30° C., respectively.

In one preferred embodiment of the present disclosure, the refrigerant temperature ranges from −16° C. to 10° C., and the refrigerant is white oil of industrial grade7#.

In one preferred embodiment of the present disclosure, the molar ratio of the phosphorus trichloride to the ethylene oxide ranges from 1:3.0 to 1:3.4.

Specifically, as an example of the present disclosure which uses microchannel to prepare tris-(2-chloroethyl)phosphite, it comprises the following steps:
(1) continuously pumping the phosphorus trichloride and the ethylene oxide into the tubular pre-mixer for pre-mixing, respectively at flow rates ranging from 200 kg/h to 600 kg/h and 200 kg/h to 600 kg/h, wherein the tubular pre-mixer comprises a static mixing pipe having a size of Ø50 mm×1000 mm; and
(2) then introducing the pre-mixed mixture of the phosphorus trichloride and the ethylene oxide into a microchannel reaction device, starting a refrigerant cooling unit of the microchannel reaction device simultaneously, and collecting an effluent from the microchannel reaction device to obtain the product tris-(2-chloroethyl)phosphite after complete reaction, wherein the temperature of the materials, the pressure, and the refrigerant temperature in the microchannel reaction device are adjusted to range from 15° C. to 30° C., 0.30 MPa to 0.80 MPa, and −16° C. to 10° C. respectively, and the residence time of the phosphorus trichloride and the ethylene oxide in the microchannel reaction device is controlled by adjusting the flow rate of the phosphorus trichloride and that of the ethylene oxide entering the tubular pre-mixer; and wherein the molar ratio of the phosphorus trichloride to the ethylene oxide ranges from 1:3.0 to 1:3.4, and the microchannel reaction device comprises 4 to 6 sets of microchannel reactors connected in series with each other, each set of the microchannel reactors comprising two hundred pipes each having a size of Ø4 mm×2000 mm.

The principle of the method of preparing tris-(2-chloroethyl)phosphite by means of microchannel reaction technology according to the present disclosure is shown as follows:

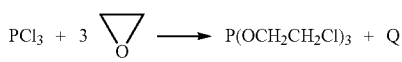

$$PCl_3 + 3\ \underset{O}{\triangledown} \longrightarrow P(OCH_2CH_2Cl)_3 + Q$$

When the above esterification reaction is carried out in a normal enamel reactor, a part of the product may polymerizes and a part of raw materials may be hydrolyzed or oxidized because of the poor mass and heat transfer effects and the long reaction time. The purity of tris-(2-chloroethyl)phosphite in the final-obtained product can only reach 90%.

The present disclosure employs the method that combines a tubular pre-mixer and a multiple-stage microchannel reactor. In a first step, after being fully pre-mixed, phosphorus trichloride and ethylene oxide are sufficiently pre-mixed inside a tubular mixer, which comprises at least one static mixing pipe of Ø50 mm×1000 mm, under a pressure ranging from 0.01 MPa to 2.00 MPa. The residence time of phosphorus trichloride and the ethylene oxide in the microchannel reaction device are controlled by adjusting the flow rates of phosphorus trichloride and ethylene oxide entering the tubular pre-mixer, respectively. In a second step, an esterification reaction occurs in the pre-mixed mixture of the phosphorus trichloride and the ethylene oxide under a pressure of 0.01 MPa-2.00 MPa inside the multiple-stage series microchannel reactors, wherein each set of the microchannel reactors comprises 50 to 500 pipes each with a size of Ø4 mm×2000 mm. Compared with an ordinary enamel reactor, the microchannel reactor has a larger heat transfer area and a higher heat and mass transfer efficiency. Accordingly, the reaction rate of the above esterification reaction carried out in a microchannel reactor would be 10 to 100 times than that of the esterification reaction carried out in a tank reactor. Meanwhile, because the whole system according to the present disclosure is closed and isolated from air, oxidation and hydrolysis of the phosphorus trichloride is avoided. Since the residence time of the esterification product in the reactor reduces from 110 hours as in tank reactor to a few minutes according to the present disclosure, the content of tris-(2-chloroethyl)phosphite in the esterification product can achieve 98% or more. For example, to a 2000 L ordinary enamel reactor 1200 kg of phosphorus trichloride and 1200 kg of ethylene oxide were introduced at a rate of 12 kg/hour over a period of 100 hours, followed by reaction under a maintained temperature for 10 hours. An esterfication product containing 90% of tris-(2-chloroethyl) phosphite was obtained after the completion of the reaction, and the total reaction time is 110 hours.

The present disclosure has the following benefits.

(1) Phosphorus trichloride and ethylene oxide are mixed in a tubular pre-mixer under a pressure ranging from 0.01 MPa to 2.00 MPa. The resulting mixture then enters multiple-stage microchannel reactors in series connection with each other for an esterification reaction. Thus the content of tris-(2-chloroethyl)phosphite rises from 90% to 98% in the esterification product, which is a significant increase.

(2) The production efficiency is 10 to 100 times higher than that of an ordinary tank reaction.

(3) As a result of the continuous reaction in the whole process, an automatic DCS control system can be used. Because the whole system is closed and isolated from air, the oxidation and hydrolysis of the phosphorus trichloride is avoided. Since the residence time of the esterification product in the reactor reduces from the 110 hours as in an ordinary tank to a few minutes (such as 1 to 5 minutes) according to the present disclosure, the content of tris-(2-chloroethyl)phosphite in the esterification product can achieve 98% or more.

The present disclosure provides a new method of preparing tris-(2-chloroethyl)phosphite which is of higher efficiency, lower costs, and higher industrial values.

BRIEF DESCRIPTION OF THE DRAWINGS

In the drawings, identical components are marked with the same number.

DETAILED DESCRIPTION OF THE EMBODIMENTS

Figure 1:
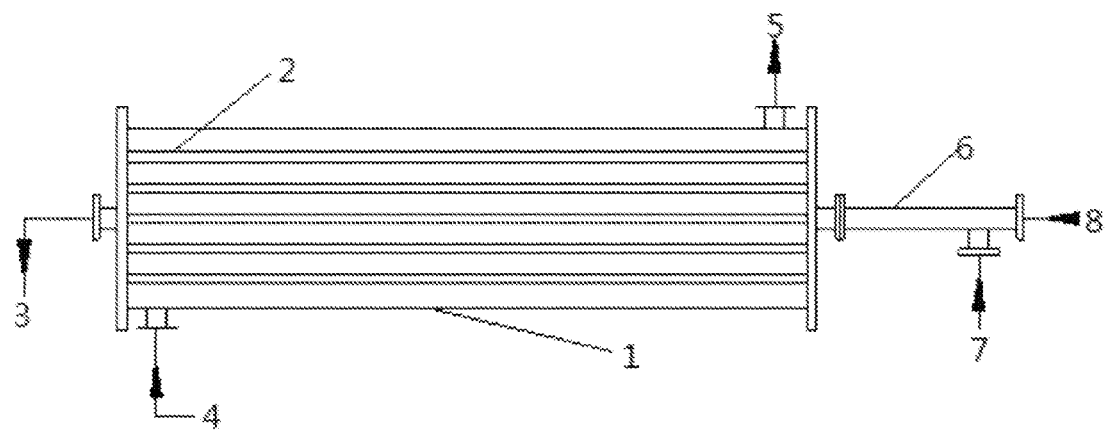
FIG. 1 is a structural diagram of a microchannel reactor.
Figure 2:
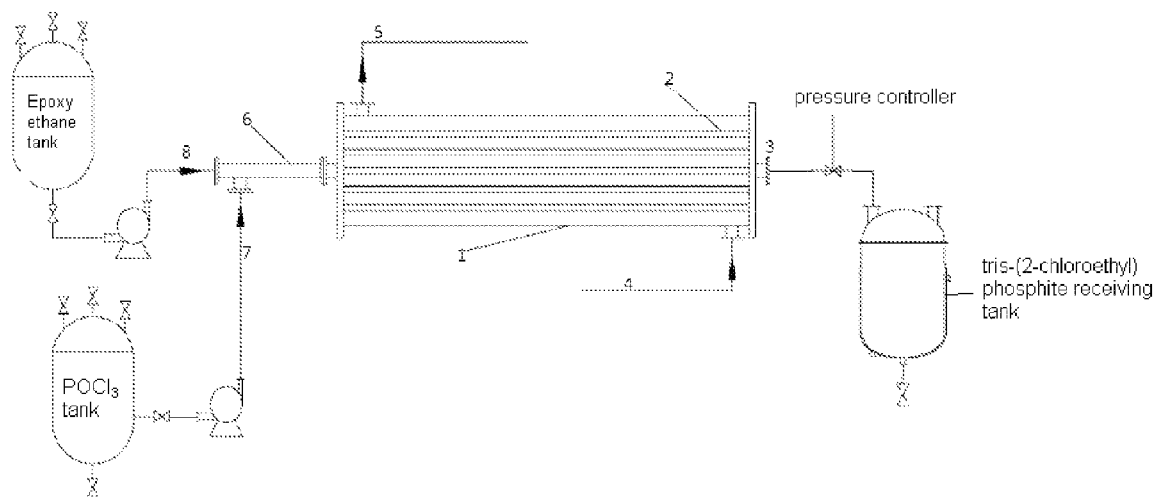
FIG. 2 is a flow chart of an experiment.

The terminology used herein is for the purpose of describing particular embodiments only and is not intended to be limiting of the present disclosure. As used herein, the singular forms "a", "an", and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, group of elements, components, and/or groups thereof.

Language such as "including", "comprising", "having", "containing", or "involving", and variations thereof, is intended to be broad and encompass the subject matter listed thereafter, as well as equivalents, and additional subject matter not recited. Further, whenever a composition, a group of elements, process or method steps, or any other expression is preceded by the transitional phrase "comprising", "including", or "containing", it is understood that it is also contemplated herein the same composition, group of elements, process or method steps or any other expression with transitional phrases "consisting essentially of", "consisting of", or "selected from the group of consisting of", preceding the recitation of the composition, the group of elements, process or method steps or any other expression.

The corresponding structures, materials, acts, and equivalents of all means or step plus function elements in the claims, if applicable, are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiments described herein were chosen and described in order to best explain the principles of the present disclosure and the practical application, and to enable others of ordinary skill in the art to understand the present disclosure for various embodiments with various modifications as are suited to the particular use contemplated. Accordingly, while the present disclosure has been described in terms of embodiments, those of skill in the art will recognize that the present disclosure can be practiced with modifications and in the spirit and scope of the appended claims.

Reference will now be made in detail to certain disclosed subject matter. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

As shown in FIG. 1, a microchannel reaction system of the present disclosure comprises a tubular pre-mixer 6 and a microchannel reaction device 1 connected in series with each other, wherein the microchannel reaction device 1 is equipped with a refrigerant cooling unit and connected to the tubular pre-mixer and the refrigerant cooling unit. The microchannel reaction device 1 is equipped with a material outlet 3, a refrigerant inlet 4, and a refrigerant outlet 5. The tubular pre-mixer 6 is equipped with two material inlets, i.e. a second material inlet 7 and a third material inlet 8. An outlet of the tubular pre-mixer communicates with an inlet of the microchannel reaction device. The tubular pre-mixer comprises a static mixing pipe with the size of Ø50 mm×1000 mm. The microchannel reaction device, as shown in FIG. 1, comprises 1 to 10 sets of microchannel reactors connected in series with each other, wherein each set of the microchannel reactors comprises 50 to 500 pipes 2 each with the size of Ø4 mm×2000 mm.

Example 1

A microchannel reaction device having two stages in series connection was used. That is, two sets of microchannel reactors were connected in series. Each set of the microchannel reactors had 200 pipes each having the size of Ø4 mm×2000 mm. The reactor had an outer diameter of 600 mm and a length of 2000 mm.

As shown in FIG. 1 (only one set of microchannel reactor was shown), phosphorus trichloride and ethylene oxide were continuously pumped into a tubular pre-mixer which comprises static mixing pipes each having the size of Ø50 mm×1000 mm, wherein the mass flow rates of phosphorus trichloride and ethylene oxide were respectively controlled at 100 kg/h. After the phosphorus trichloride and the ethylene oxide were premixed in the tubular pre-mixer, a mixed liquor thereof then entered the microchannel reaction device having two stages in series connection for an exothermic reaction. At the same time, a refrigerant cooling unit (the refrigerant is 7# industrial white oil) coupled with the microchannel reaction device was started for cooling, wherein the refrigerant temperature was in a range from −16 to 10° C. The materials within the microchannel reactors were controlled, by an outlet of a counterbalance valve arranged in a last stage microchannel reactor, to have a temperature of 10-15° C., a pressure of 0.30 MPa, and a residence time in the microchannel of 125 seconds. A product containing 98.8% of tris-(2-chloroethyl)phosphite was stably obtained at an outlet of the last stage microchannel reactor at a flow rate of 200 kg/h.

Example 2

A microchannel reaction device having four stages in series connection was used. That is, four sets of microchannel reactors were connected in series. Each set of the microchannel reactors had 250 pipes each having the size of Ø4 mm×2000 mm. The reactor had an outer diameter of 600 mm and a length of 2000 mm.

Phosphorus trichloride and ethylene oxide were continuously pumped into a tubular pre-mixer which comprises static mixing pipes each having the size of Ø50 mm×1000 mm, wherein the mass flow rates of phosphorus trichloride and ethylene oxide were respectively controlled at 300 kg/h. After the phosphorus trichloride and the ethylene oxide were premixed in the tubular pre-mixer, a mixed liquor thereof then entered the microchannel reaction device having four stages in series connection for an exothermic reaction. At the same time, a refrigerant cooling unit (the refrigerant is 7# industrial white oil) coupled with the microchannel reaction device was started for cooling, wherein the refrigerant temperature was in a range from −16 to 10° C. The materials within the microchannel reactors were controlled, by an outlet of a counterbalance valve arranged in a last stage microchannel reactor, to have a temperature of 15-20° C., a pressure of 0.50 MPa, and a residence time in the microchannel of 104 seconds. A product containing 98.3% of tris-(2-chloroethyl)phosphite was stably obtained at an outlet of the last stage microchannel reactor at a flow rate of 600 kg/h.

Example 3

A microchannel reaction device having six stages in series connection was used. That is, six sets of microchannel reactors were connected in series. Each set of the microchannel reactors had 300 pipes each having the size of Ø4 mm×2000 mm. The reactor had an outer diameter of 600 mm and a length of 2000 mm.

Phosphorus trichloride and ethylene oxide were continuously pumped into a tubular pre-mixer which comprises static mixing pipes each having the size of Ø50 mm×1000 mm, wherein the mass flow rates of phosphorus trichloride and ethylene oxide were respectively controlled at 500 kg/h. After the phosphorus trichloride and the ethylene oxide were premixed in the tubular pre-mixer, a mixed liquor thereof then entered the microchannel reaction device having six stages in series connection for an exothermic reaction. At the same time, a refrigerant cooling unit (the refrigerant is 7# industrial white oil) coupled with the microchannel reaction device was started for cooling, wherein the refrigerant temperature was in a range from −16 to 10° C. The materials within the microchannel reactors were controlled, by an outlet of a counterbalance valve arranged in a last stage microchannel reactor, to have a temperature of 20-25° C., a pressure of 0.70 MPa, and a residence time in the microchannel of 112 seconds. A product containing 98.6% of tris-(2-chloroethyl)phosphite was stably obtained at an outlet of the last stage microchannel reactor at a flow rate of 1000 kg/h.

Example 4

A microchannel reaction device having eight stages in series connection was used. That is, eight sets of microchannel reactors were connected in series. Each set of the microchannel reactors had 400 pipes each having the size of Ø4 mm×2000 mm. The reactor had an outer diameter of 600 mm and a length of 2000 mm.

Phosphorus trichloride and ethylene oxide were continuously pumped into a tubular pre-mixer which comprises static mixing pipes each having the size of Ø50 mm×1000 mm, wherein the mass flow rates of phosphorus trichloride and ethylene oxide were respectively controlled at 700 kg/h. After the phosphorus trichloride and the ethylene oxide were pre-mixed in the tubular pre-mixer, a mixed liquor thereof then entered the microchannel reaction device having eight stages in series connection for an exothermic reaction. At the same time, a refrigerant cooling unit (the refrigerant is 7# industrial white oil) coupled with the microchannel reaction device was started for cooling, wherein the refrigerant temperature was in a range from −16 to 10° C. The materials within the microchannel reactors were controlled, by an outlet of a counterbalance valve arranged in a last stage microchannel reactor, to have a temperature of 25-30° C., a pressure of 1.00 MPa, and a residence time in the microchannel of 142 seconds. A product containing 98.8% of tris-(2-chloroethyl)phosphite was stably obtained at an outlet of the last stage microchannel reactor at a flow rate of 1400 kg/h.

Example 5

A microchannel reaction device having ten stages in series connection was used. That is, ten sets of microchannel reactors were connected in series. Each set of the microchannel reactors had 500 pipes each having the size of Ø4 mm×2000 mm. The reactor had an outer diameter of 600 mm and a length of 2000 mm.

Phosphorus trichloride and ethylene oxide were continuously pumped into a tubular pre-mixer which comprises static mixing pipes each having the size of Ø50 mm×1000 mm, wherein the mass flow rates of phosphorus trichloride and ethylene oxide were respectively controlled at 1000 kg/h. After the phosphorus trichloride and the ethylene oxide were premixed in the tubular pre-mixer, a mixed liquor thereof then entered the ten-stage microchannel reactors in series connection for an exothermic reaction. At the same time, a refrigerant cooling unit (the refrigerant is 7# industrial white oil) coupled with the microchannel reaction device was started for cooling, wherein the refrigerant temperature was in a range from −16 to 10° C. The materials within the microchannel reactors were controlled, by an outlet of a counterbalance valve arranged in a last stage microchannel reactor, to have a temperature of 35-40° C., a pressure of 2.00 MPa, and a residence time in the microchannel of 156 seconds. A product containing 98.4% of tris-(2-chloroethyl)phosphite was stably obtained at an outlet of the last stage microchannel reactor at a flow rate of 2000 kg/h.

Comparative Example 1

A 2000 L ordinary enamel reactor was charged with 1200 kg of phosphorus trichloride, and a total amount of 1200 kg of ethylene oxide at a rate of 12 kg/h over a period of 100 hours, followed by reaction at a maintained temperature for 10 hours. After the completion of the reaction, 2400 kg of an esterification product containing 90% of tris-(2-chloroethyl)phosphite was obtained. The reaction time was 110 hours in total. It can be calculated that 21.8 kg of the esterification product can be obtained per hour.

The results of examples 1-5 and the comparative example indicate, compared to the comparative example, the method of the present disclosure not only greatly reduces the reaction time and improves the reaction efficiency, but also enables the acquisition of a product having a higher content of tris-(2-chloroethyl)phosphite, thus improving the quality of the product and the usage rate of raw materials.

As will be appreciated by one skilled in the art, the foregoing functions and/or process may be embodied as a system, method or computer program product. For example, the functions and/or process may be implemented as computer-executable program instructions recorded in a computer-readable storage device that, when retrieved and executed by a computer processor, controls the computing system to perform the functions and/or process of embodiments described herein. In one embodiment, the computer system can include one or more central processing units, computer memories (e.g., read-only memory, random access memory), and data storage devices (e.g., a hard disk drive). The computer-executable instructions can be encoded using any suitable computer programming language (e.g., C++, JAVA, etc.). Accordingly, aspects of the present disclosure may take the form of an entirely software embodiment (including firmware, resident software, micro-code, etc.) or an embodiment combining software and hardware aspects.

It should be noted that the above examples are only used to explain, rather than to limit the present disclosure in any manner. Although the present disclosure has been discussed with reference to preferable examples, it should be understood that the terms and expressions adopted are for describing and explaining instead of limiting the present disclosure. The present disclosure can be modified within the scope of the claims, and can be amended without departing from the scope or spirits of the present disclosure.

The invention claimed is:

1. A method of preparing tris-(2-chloroethyl)phosphite, comprising the steps of:
    continuously pumping phosphorus trichloride and ethylene oxide into a tubular pre-mixer for pre-mixing, respectively, at a mixing pressure in a range from 0.01 MPa to 2.00 MPa, to achieve sufficient mixing of and contact between the phosphorus trichloride and the ethylene oxide; and
    introducing the pre-mixed mixture of the phosphorus trichloride and the ethylene oxide into a microchannel reaction device, and starting a refrigerant cooling unit of the microchannel reaction device simultaneously, to obtain a product tris-(2-chloroethyl)phosphite after complete reaction.

2. The method according to claim 1, wherein the temperature of the materials, the pressure, and the molar ratio of the phosphorus trichloride to the ethylene oxide in the microchannel reaction device range from 0° C. to 50° C., 0.01 MPa to 2.00 MPa, and 1:3.0 to 1:3.8, respectively.

3. The method according to claim 1, wherein the microchannel reaction device comprises 1 to 10 sets of microchannel reactors connected in series with each other.

4. The method according to claim 1, wherein the phosphorus trichloride and the ethylene oxide enter the tubular pre-mixer at flow rates ranging from 100 kg/h to 1000 kg/h and 100 kg/h to 1000 kg/h, respectively.

5. The method according to claim 3, wherein each set of the microchannel reactors comprises 50 to 500 pipes each having a size of Ø4 mm×2000 mm.

6. The method according to claim 1, wherein the microchannel reaction device comprises three to five sets of microchannel reactors connected in series with each other, each set of the microchannel reactors comprising one hundred to three hundred pipes each having a size of Ø4 mm×2000 mm.

7. The method according to claim 2, wherein the reaction pressure is in a range from 0.30 MPa to 0.80 MPa, and the reaction temperature is in a range from 15° C. to 30° C.

8. The method according to claim 1, wherein the refrigerant temperature within the refrigerant cooling unit is in a range from −16° C. to 10° C.

9. The method according to claim 1, wherein the molar ratio of the phosphorus trichloride to the ethylene oxide is in a range from 1:3.0 to 1:3.4.

10. The method according to claim 1, wherein the method is performed in accordance with the steps of:
   first continuously pumping the phosphorus trichloride and the ethylene oxide into the tubular pre-mixer for pre-mixing, respectively at the flow rates ranging from 200 kg/h to 600 kg/h and 200 kg/h to 600 kg/h, wherein the tubular pre-mixer comprises a static mixing pipe having a size of Ø50 mm×1000 mm; and
   then introducing the pre-mixed mixture of the phosphorus trichloride and the ethylene oxide into a microchannel reaction device, starting a refrigerant cooling unit of the microchannel reaction device simultaneously, and collecting an effluent from the microchannel reaction device to obtain the product tris-(2-chloroethyl)phosphite after complete reaction, wherein the temperature of the materials, the pressure, and the refrigerant temperature in the microchannel reaction device are adjusted to range from 15° C. to 30° C., 0.30 MPa to 0.80 MPa, and −16° C. to 10° C. respectively, and the residence time of the phosphorus trichloride and the ethylene oxide in the microchannel reaction device is controlled by means of adjusting the flow rate of the phosphorus trichloride and that of the ethylene oxide entering the tubular pre-mixer, and wherein the molar ratio of the phosphorus trichloride to the ethylene oxide is in a range from 1:3.0 to 1:3.4, and the microchannel reaction device comprises 4 to 6 sets of microchannel reactors connected in series with each other, each set of the microchannel reactors comprising two hundred pipes each having a size of Ø4 mm×2000 mm.

\* \* \* \* \*